United States Patent [19]

Yamada

[11] Patent Number: 4,770,523
[45] Date of Patent: Sep. 13, 1988

[54] APPARATUS FOR MEASURING CURVATURE

[75] Inventor: Kenji Yamada, Narashino, Japan

[73] Assignee: Nippon Kogaku K. K., Tokyo, Japan

[21] Appl. No.: 818,658

[22] Filed: Jan. 14, 1986

[30] Foreign Application Priority Data

Jan. 25, 1985 [JP] Japan .................................. 60-12202

[51] Int. Cl.[4] .............................................. A61B 3/10
[52] U.S. Cl. ..................................... 351/212; 351/211; 351/247; 356/376
[58] Field of Search ............... 351/205, 206, 211, 212, 351/247; 128/303.1; 356/124, 125, 126, 376

[56] References Cited

U.S. PATENT DOCUMENTS

| | | | |
|---|---|---|---|
| 4,019,813 | 4/1977 | Cornsweet et al. | 351/212 |
| 4,315,672 | 2/1982 | Muller et al. | 351/212 |
| 4,439,025 | 3/1984 | Smirmaul | 351/212 |
| 4,440,477 | 4/1984 | Schachar | 351/212 |
| 4,540,254 | 9/1985 | Humphrey | 351/212 |
| 4,572,628 | 2/1986 | Nohda | 351/212 |
| 4,597,648 | 7/1986 | Feldon et al. | 351/205 |
| 4,606,623 | 8/1986 | Schachar | 351/212 |

Primary Examiner—Rodney B. Bovernick
Assistant Examiner—Jay Ryan
Attorney, Agent, or Firm—Shapiro and Shapiro

[57] ABSTRACT

Apparatus for measuring curvature of an object automatically is so composed to guide two radiation beams reflected by the object to a linear image sensor, and determine the curvature of the object from the signals obtained from the linear image sensor, in response to the distance of two radiation beams on the sensor. The apparatus is further provided with an image rotator between means for generating two radiation beams and the object.

10 Claims, 5 Drawing Sheets

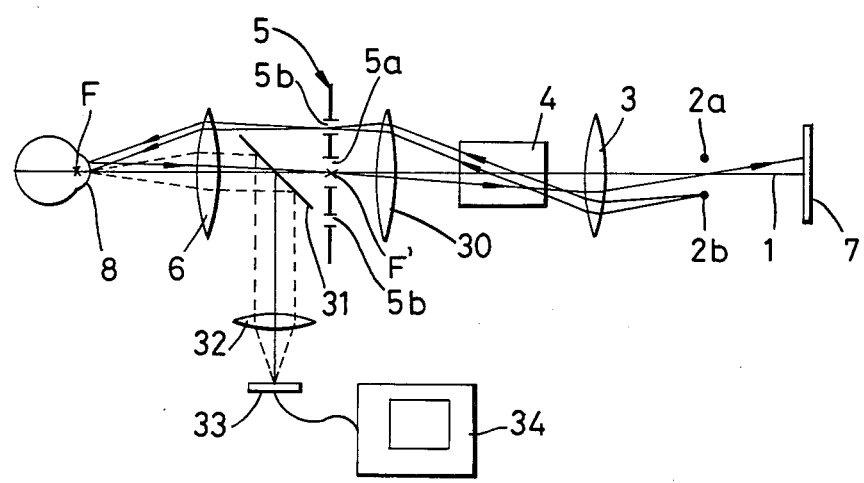
F I G. 8

APPARATUS FOR MEASURING CURVATURE

BACKGROUND OF THE INVENTION

1. Field of the Invention

The present invention relates to an apparatus for automatically measuring curvature of an object such as a cornea.

2. Description of the Prior Art

A similar apparatus is already disclosed in the Japanese Patent Laid-open No. 125302/1982. In such known apparatus, light from an annular light source is projected onto a cornea, and an oval image formed by the reflected light is received by a linear image sensor, and the curvature of the cornea is determined from the length of image sensor receiving said oval image. However such apparatus is associated with a drawback that an error will result in case the center of the oval image is not positioned on the image sensor. Also the Japanese Patent Laid-open No. 54927/1983 discloses another structure in which five image sensors are radially arranged to determine the oval shape and a rotating mechanism is eliminated in order to avoid the aforementioned drawback. However such structure is associated with a drawback of requiring a complicated electric circuitry and generating an error in case the surface of the cornea is not toric, since the principle of measurement is based on an assumption that the cornea has a toric surface.

Besides such conventional apparatus require a special annular light source.

SUMMARY OF THE INVENTION

In consideration of the foregoing, an object of the present invention is to provide an apparatus not associated with the aforementioned drawbacks and capable of automatically measuring the curvature with a high precision, by means of a simple structure.

The above-mentioned object can be achieved, by the apparatus of the present invention, by guiding two radiation beams reflected by an object to a linear image sensor, and determining the curvature of the object from the signals obtained from said linear image sensor, in response to the distance of two radiation beams on said sensor. The apparatus of the present invention is further provided with an image rotator, between means for generating two radiation beams and the object to be measured.

BRIEF DESCRIPTION OF THE DRAWINGS

FIG. 8 is a schematic view of an optical system constituting a second embodiment of the present invention.

DESCRIPTION OF THE PREFERRED EMBODIMENTS

Now the present invention will be clarified in detail by embodiments thereof shown in the attached drawings.

Figure 2A:
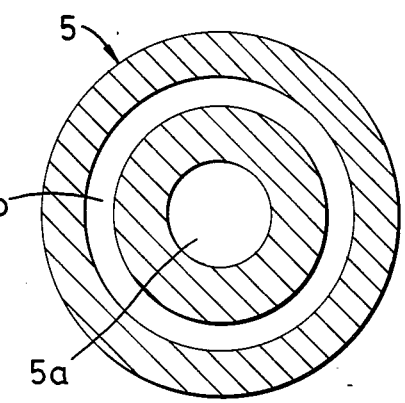
FIG. 2A is a plan view of a diaphragm plate to be employed in the optical system shown in FIG. 1.
Figure 2B:
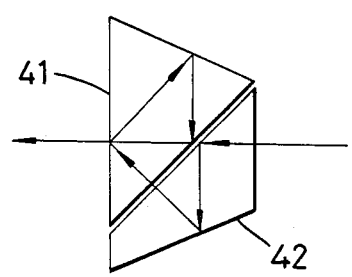
FIGS. 2B and 2C are schematic views showing the structure of an image rotator.
Figure 2C:
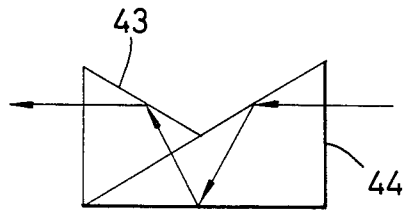

Symmetrically across an optical axis 1, there are provided slit-shaped light sources 2a, 2b extending perpendicularly to the plane of the drawing. In front of said light sources there is provided a relay lens 3, in front of which there is provided an image rotator 4. In front of said image rotator 4 there is provided a diaphragm plate 5 which, as shown in FIG. 2A, is provided with a central translucent portion 5a and an annular translucent portion 5b, both concentric with the optical axis 1. Hatched areas in FIG. 2A are opaque. The image rotator 4 is composed, as shown in FIG. 2B or 2C, of a combination of prisms 41, 42 or a combinations of prisms 43, 44. In front of said diaphragm plate 5 there is provided an objective lens 6 of which the rear focal point is positioned on the diaphragm plate 5. Behind the slit-shaped light sources 2a, 2b there is provided a linear image sensor 7 which lies in the plane of the drawing perpendicularly to the optical axis 1 in such a manner that said optical axis crosses the approximate center of the light-receiving face.

Figure 3:
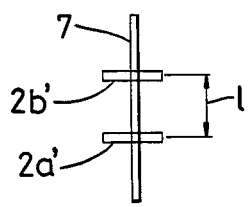
FIG. 3 is a schematic view showing images of slit-shaped light sources formed on a linear image sensor, as seen from a direction P shown in FIG. 1.

Thus the light beams from the light sources 2a, 2b pass through the relay lens 3 and image rotator 4 and focused on the annular translucent portion 5b of the diaphragm plate 5. Said beams are then converted into parallel beams by the objective lens 6, and projected onto an object (a cornea in this case) 8 in front of the objective lens 6. The beams reflected by the surface of cornea 8 are focused between the diaphragm plate 5 and relay lens 3 by means of the objective lens 6, and focused again on the linear image sensor 7 by means of the image rotator 4 and relay lens 3. FIG. 3 shows the images 2a', 2b' of the slit-shaped light sources focused on the image sensor 7, and the space 1 between said images 2a', 2b' is proportional to the curvature of cornea 8 in the longitudinal direction containing the plane of the drawing.

Rotation of the image rotator 4 about the optical axis 4 generates an effect to the cornea 8 as if the slit-shaped light sources 2a, 2b and the linear image sensor 7 are integrally rotated about the optical axis 1. It is therefore possible to measure the curvatures in different longitudinal directions and to detect astigmatism of the cornea by measuring the space 1 between the images 2a', 2b' on the linear image sensor 7 at different rotational positions of the image rotator 4.

Figure 1:
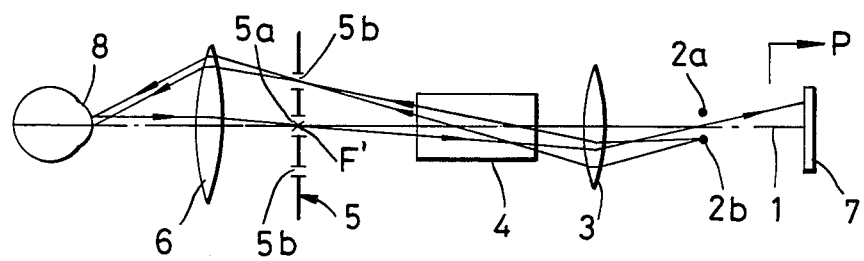
FIG. 1 is a schematic view of an optical system constituting a first embodiment of the present invention.
Figure 4:
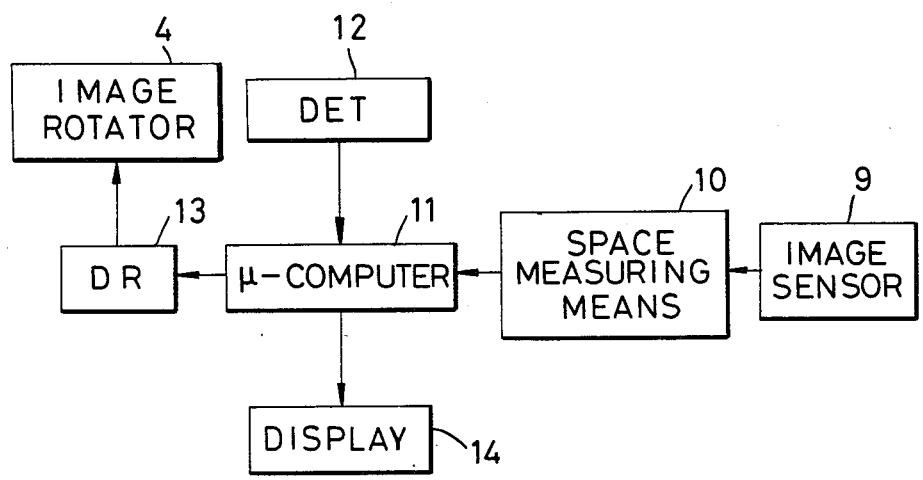
FIG. 4 is a block diagram of an electric system to be employed in connection with the optical system shown in FIG. 1.
Figure 6:
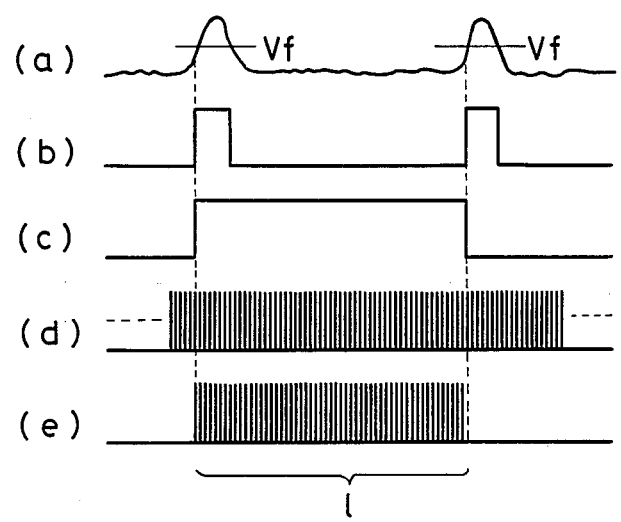
FIG. 6 is a timing chart showing the function of the apparatus of the present invention.

FIG. 4 shows an electric system to be employed in combination with the optical system shown in FIG. 1. Signals from image sensor means 9 including the linear image sensor 7 (cf. FIG. 6(a)) are supplied to space measuring means 10, which is provided with a wave shaping circuit for converting the aforementioned signals of FIG. 6(a) into signals shown in FIG. 6(b) according to a suitable threshold level Vf; a flip-flop which is set at the start of a signal of FIG. 6(b) and is reset at the start of a succeeding signal to produce an output signal as shown in FIG. 6(c); a pulse generator for providing clock pulses as shown in FIG. 6(d); an AND gate for receiving the signals shown in FIG. 6(c) and FIG. 6(d) to output clock pulses as shown in FIG. 6(e) only when the signal of FIG. 6(c) is at the high level; and a counter for counting the number of pulses shown in FIG. 6(e), corresponding to the space between the images 2a', 2b' of light sources on the linear image sensor 7. The count of said counter is employed as the output of the space measuring means 10 and is supplied to a microcomputer 11, which receives an initial position signal from an initial position detecting device 12 for the image rotator 4, supplies a drive signal to a pulse driving device 13 for intermittently driving the image rotator 4 and displays the measured value on display means 14. The pulse driving device 13 is provided with a support member for rotatably supporting the image rotator 4 about the optical axis 1; a stepping motor for rotating said support member; and a transmitting member, for example gears, for transmitting the rotation of said stepping motor to said support member.

Figure 5:
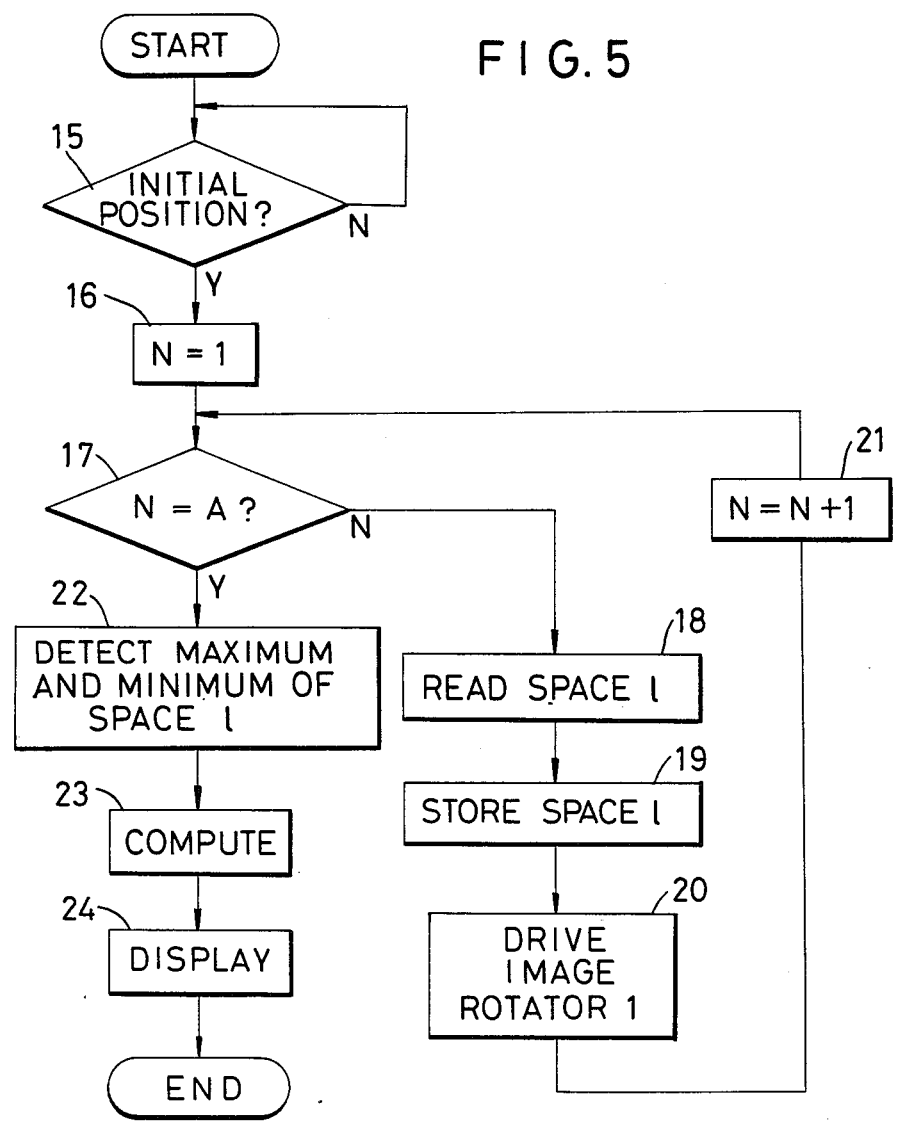
FIG. 5 is a flow chart showing the function of a microcomputer.

Now reference is made to a flow chart shown in FIG. 5 for explaining the function of the microcomputer 11. At first, in a step 15, the microcomputer 11 identifies, by means of the signal from the initial position detecting device 12, whether the image rotator 4 is in an initial position. If it is in the initial position, a step 16 sets "1" as the number of measurements N, and a step 17 identifies whether the number N of measurements has become equal to a determined value A. Since N=1 in this state, the program proceeds to a step 18 for reading the space 1 between the images 2a', 2b' of light sources, by means of the space measuring means 10. A succeeding step 19 stores thus measured space 1 in combination with the number of measurements N=1 in an internal memory. Then a step 20 supplies a drive signal to the pulse driving device 13 for rotating the image rotator 4 by a determined angle, for example 1°. The pulse driving device 13, including a stepping motor etc., rotates the image rotator 4 by 1°. The microcomputer 11 sets the number of measurements N=2 in the step 21, and repeats the steps 17, 18, 19, 20 and 21. When the number N of measurements reaches the determined value A, a step 22 identifies the maximum and minimum values of the space and the corresponding ordinal numbers of measurements stored in the step 19. The rotational angle of the image rotator 4 from the initial position, or the direction of longitudinal direction at which the measurement is carried out, can be determined from the number of measurements from the initial position. Then, in a step 23, the microcomputer 11 calculates the curvature and astigmatism of the cornea 8 from the data read in the step 22, and displays the results of calculation on the display means 14 in a step 24.

The foregoing embodiment, employing a telecentric optical system in which the diaphragm plate 5 is positioned at the rear focal point of the objective lens 6, and employing parallel light beams for irradiating the cornea 8, enables exact measurement even if the cornea 8 is somewhat displaced in the axial direction closer to or farther from the objective lens 6, since the position of a principal ray remains the same on the linear image sensor and such displacement only causes certain blurring of the images 2a', 2b'. However such telecentric optical system can be dispensed with if the distance between the cornea 8 and the objective lens 6 can always be precisely maintained.

Also an eventual displacement of the cornea 8 in a direction perpendicular to the optical axis 1 only causes a parallel displacement of the image 2a', 2b' in lateral and/or vertical direction on the linear image sensor 7 without any change in the space of said images, and the displacement of the image of a light source out of the linear image sensor 7, as in the case of employing a point light source, does not occur in the structure of the present invention.

The initial position detecting device 12 shown in FIG. 4 can be of various structures. As an example, there may be employed a slit member rotating integrally with the image rotator 4, provided with a slit corresponding to the initial position and positioned between a light and a photodetector, whereby an electric signal exceeding a determined level can be obtained from the photodetector only when the image rotator 4 is in the initial position in which said slit is positioned between said light source and photodetector. Naturally such photoelectric detection can be easily replaced by mechanical detection, for example employing a limit switch.

In response to a rotation of the image rotator 4 by an angle, the images rotate by a doubled angle, and the direction of irradiation needs to be varied over a range of 180° in order to obtain information over the entire longitudinal range of the object 8. It is therefore possible to achieve continuous measurements with the microcomputer 11 by employing a synchronous motor for driving the image rotator 4 and providing photoelectric or magnetic rotary encoders for generating an initial position signal at each interval of 90° and reading signals from said encoders and from the space measuring means 10 in synchronization. In such case the signals for intermittently driving the image rotator 4 are no longer required.

Figure 7:
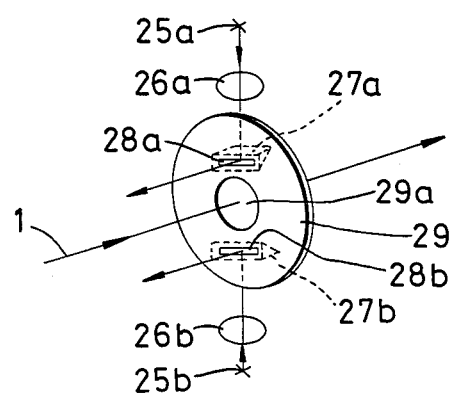
FIG. 7 is a perspective view of another example of slit-shaped light sources to be employed in the optical system of FIG. 1.

The slit-shaped light sources 2a, 2b shown in FIG. 1 can be directly composed for example of light-emitting diodes, or can be derived from another optical system for example through half mirrors positioned between the relay lens 3 and the linear image sensor 7. However, in order to avoid loss in the amount of light in the latter case, there is preferably employed a structure shown in FIG. 7, in which light beams emitted toward the optical axis from light sources 25a, 25b positioned symmetrically about the optical axis are converged by collector lenses 26a, 26b, then deflected by small prisms 27a, 27b in a direction approximately parallel to the optical axis and illuminate slits 28a, 28b performing a function similar to that of the slit-shaped light sources 2a, 2b shown in FIG. 1. The structure shown in FIG. 7 is composed of a glass plate 29 on which a metal layer is deposited in such a manner as to transmit the light only in two slits 28a, 28b and a central portion 29a for the measuring light beam and to intercept the light in other areas, and on which the small prisms 27a, 27b are adhered behind said slits 28a, 28b. In this structure it is possible to minimize the entry of the light reflected from optical members into the linear image sensor 7, since the collector lenses 26a, 26b can suitably regulate the extent of light beams from the slits 28a, 28b to avoid unnecessary scattering. Said central portion 29a is free from metal deposition in order to transmit the light reflected by the cornea 8.

Now reference is made to FIG. 8 for explaining a second embodiment of the present invention. An optical system of the second embodiment shown in FIG. 8 is different from that shown in FIG. 1 in that a monitor optical system is added in order to bring the cornea 8 and the apparatus to a correct mutual positional relationship.

More specifically, a viewing field lens 30 is provided between the image rotator 4 and the diaphragm plate 5, and the slit-shaped light sources 2a, 2b are rendered conjugate with the annular translucent portion 5b of the diaphragm 5 with respect to the relay lens 3 and the viewing field lens 30. The illuminating beams constitute telecentric beams parallel to the optical axis 1 between said lenses 30 and 6 and irradiate positions close to the front focal point F of the objective lens 6. Said front focal point F is conjugate with the linear image sensor 7 with respect to the objective lens 6, viewing field lens 30 and relay lens 3. Between the objective lens 6 and the diaphragm plate 5 there is diagonally provided a partially translucent mirror 31, such as a holed mirror, and the light reflected by said mirror 31 is focused, through a monitor lens 32, onto an image sensor 33. Said image sensor 33 is positioned on the rear focal point of the monitor lens 32 and is therefore conjugate with the front focal point F of the objective lens 6. The output signals of said image sensor 33 are displayed visually on a television monitor 34.

Thus the linear image sensor 7 can be correctly focused to the false images of the slit-shaped light sources 2a, 2b, generated by reflection by cornea 8, by moving the apparatus to achieve focusing to said images on the television monitor 34. Said viewing field lens 30 and the objective lens 6 constitute an objective lens system.

Said partially translucent mirror 31 can also be composed of a half mirror, or a dichroic mirror separating the measuring light and the observing light through a difference in wavelength.

It is furthermore possible to compose said partially translucent mirror 31 by a so-called cold mirror which is a dichroic mirror transmitting far infrared light for measurement and reflecting other light components, and to provide another dichroic mirror diagonally between the cold mirror 31 and the monitor lens 32 for transmitting near infrared light for monitoring on television and to reflect visible light, whereby an index mark to be observed by the eye to be inspected is projected to said eye through the dichroic mirror, cold mirror 31 and objective lens 6 and a focusing mark is focused onto the image sensor 33 through the rear face of said dichroic mirror. In this manner it is possible to fix the eye to be inspected and to easily achieve focusing and positioning through said mark displayed on the monitor television 34.

The apparatus of the present invention, capable of measurements at as many positions as desired, can measure an averaged toric surface, even when the measured object is not toric, by detecting the aberrations from the toric surface. Also a special annular light source is not required, and a sufficient amount of light can be obtained from ordinary light sources such as filaments or light-emitting diodes.

What is claimed is:

1. An apparatus for measuring curvature of a cornea provided at a determined position on a reference axis, comprising:
   (a) an objective lens component having an optical axis substantially corresponding with said reference axis;
   (b) irradiating means positioned opposite to said determined position with respect to said objective lens component, said irradiating means emitting two radiation beams toward said objective lens component so that said two radiation beams are positoned symmetrically with respect to said reference axis, said irradiating means having means for causing each of said two radiation beams to extend in a direction which is substantially perpendicular to a direction of separation of said two radiation beams on a plane perpendicular to said reference axis;
   (c) linear image sensor means positioned opposite to said objective lens component with respect to said irradiating means, said linear image sensor means having a radiation receiving surface and producing an output signal conforming to the intensity distribution of radiation on said radiation receiving surface;
   (d) an optical member disposed between said irradiating means and said objective lens component so that said two radiation beams are transferred to the cornea at said determined position through said optical member and said objective lens component, so that said two radiation beams are reflected by the cornea, and so that the reflected radiation beams are transferred to said radiation receiving surface through said objective lens component and said optical member, said optical member being rotatable about said reference axis;
   (e) driving means for rotating said optical member about said reference axis so that positions of said two radiation beams are rotated about said reference axis integrally without changing the positional relationship of said irradiating means and said image sensor means; and
   (f) detecting means responsive to said output signal for detecting a space between said reflected beams on said radiation receiving surface and producing a detection signal indicative of the detected space.

2. An apparatus according to claim 1, which further comprises memory means and control means that causes said driving means to repeatedly rotate said optical member by a predetermined angle and that causes said detecting means to store said detection signal in said memory means every rotation of said optical member by said predetermined angle.

3. An apparatus according to claim 2, wherein said control means causes said driving means to rotate said optical member from an initial position by 180°.

4. An apparatus according to claim 3, wherein said control means calculates astigmatism of the cornea in response to the content of said memory means.

5. An apparatus for measuring curvature of an object provided at a determined position on a reference axis, comprising:
   (a) an objective lens component having an optical axis substantially corresponding with said reference axis;
   (b) irradiating means positioned opposite to said determined position with respect to said objective lens component, said irradiating means emitting two radiation beams toward said objective lens component so that said two radiation beams are positioned symmetrically with respect to said reference axis;
   (c) linear image sensor means positioned opposite to said objective lens component with respect to said irradiating means, said linear image sensor means having a radiation receiving surface and producing an output signal conforming to the intensity distribution of radiation on said radiation receiving surface;

(d) an optical member disposed between said irradiating means and said determined position so that said two radiation beams are transferred to the object at said determined position through said optical member and said objective lens component, so that said two radiation beams are reflected by the object, and so that the reflected radiation beams are transferred to said radiation receiving surface through said objective lens component and said optical member, said optical member being rotatable about said reference axis;

(e) driving means for rotating said optical member about said reference axis so that positions of said two radiation beams are rotated about said reference axis integrally without changing the positional relationship of said irradiating means and said image sensor means; and (f) means responsive to said output signal for calculating curvature of the object.

6. An apparatus according to claim 5, wherein each of said two radiation beams extends in a direction which crosses a direction of separation of said two radiation beams on a plane perpendicular to said reference axis.

7. An apparatus according to claim 6, wherein said optical member is disposed between said irradiating means and said objective lens component.

8. An apparatus according to claim 7, which further comprises a diaphragm plate having a radiation shielding area and a radiation transferring area surrounded by said radiation shielding area, wherein said diaphragm plate is disposed between said objective lens component and said optical member so that said optical axis passes through said radiation transferring area and said diaphragm plate is perpendicular to said reference axis.

9. An apparatus according to claim 8, wherein said two radiation beams are transferred to the object through an area opposite to said radiation transferring area with respect to said radiation shielding area and said reflected radiation beams are transferred to said linear image sensor means through said radiation transferring area.

10. An apparatus for measuring curvature of an object provided at a determined position on a reference axis, comprising:

(a) an objective lens component having an optical axis substantially corresponding with said reference axis;

(b) irradiating means positioned opposite to said determined position with respect to said objective lens component, said irradiating means emitting a radiation beam toward said objective lens component, said radiation beam on a plane perpendicular to said reference axis extending in a direction which is perpendicular to a direction perpendicular to said reference axis;

(c) linear image sensor means positioned opposite to said objective lens component with respect to said irradiating means, said linear image sensor means having a radiation receiving surface and producing an output signal conforming to the intensity distribution of the radiation on said radiation receiving surface;

(d) an optical member disposed between said irradiating means and said determined position so that said radiation beam is transferred to the object at said determined position through said optical member and said objective lens component, so that said radiation beam is reflected by the object, and so that the reflected radiation beam is transferred to said radiation receiving surface through said objective lens component and said optical member, said optical member being rotatable about said reference axis;

(e) driving means for rotating said optical member about said reference axis so that a position of said radiation beam is rotated about said reference axis without changing the positional relationship of said irradiating means and said image sensor means; and (f) means responsive to said output signal for calculating curvature of the object provided at said determined position.

* * * * *